(12) United States Patent
Venburg et al.

(10) Patent No.: US 9,040,460 B2
(45) Date of Patent: *May 26, 2015

(54) SYNERGISTIC COMBINATION TO IMPROVE GRAPE COLOR AND TO ALTER SENSORY CHARACTERISTICS OF WINE

(75) Inventors: Gregory D. Venburg, Deerfield, IL (US); Rick Hopkins, Fresno, CA (US); Johnny A. Lopez, Lubbock, TX (US); Prem Warrior, Green Oaks, IL (US); Andrew Rath, Tasmania (AU); Schalk Reynolds, Grayslake, IL (US); Peter D. Petracek, Grayslake, IL (US)

(73) Assignee: Valent BioSciences Corporation, Libertyville, IL (US)

( * ) Notice: Subject to any disclaimer, the term of this patent is extended or adjusted under 35 U.S.C. 154(b) by 1330 days.

This patent is subject to a terminal disclaimer.

(21) Appl. No.: 12/266,633

(22) Filed: Nov. 7, 2008

(65) Prior Publication Data

US 2009/0124503 A1 May 14, 2009

Related U.S. Application Data

(60) Provisional application No. 60/986,339, filed on Nov. 8, 2007.

(51) Int. Cl.
| | | |
|---|---|---|
| *A01N 37/00* | (2006.01) | |
| *A01N 49/00* | (2006.01) | |
| *A01N 57/10* | (2006.01) | |
| *A01N 57/18* | (2006.01) | |
| *A01N 37/42* | (2006.01) | |
| *A23L 1/27* | (2006.01) | |

(52) U.S. Cl.
CPC ............... *A01N 37/42* (2013.01); *A01N 49/00* (2013.01); *A23L 1/27* (2013.01)

(58) Field of Classification Search
USPC .......................................... 504/320, 127, 142
See application file for complete search history.

(56) References Cited

U.S. PATENT DOCUMENTS

| | | | |
|---|---|---|---|
| 5,716,629 A | 2/1998 | Robertson et al. | |
| 2005/0198896 A1 | 9/2005 | Quaghebeur | |
| 2007/0265166 A1* | 11/2007 | Bardella et al. | 504/357 |

OTHER PUBLICATIONS

Wolf, T.K., Shoot Topping and Ethephon Effects on White Riesling Grapes and Grapevines, 1990, American Journal of Enology and Viticulture, vol. 41, pp. 330-341.*
Peppi, M. Cecilia, Abscisic Acid Application Timing and Concentration Affect Firmness, Pigmentation and Color of 'Flame Seedless' Grapes, 2006, HortScience, vol. 41, Issue 6, pp. 1440-1445.*
Fidelibus, Matthew, Abscisic Acid: A Potential Tool for Improving the Color of Table Grapes, 2006, Abstract, Proceedings 33rd PGRSA Annual Meeting, p. 92.*
Coombe, B. G., The Hormone Content of Repening Grape Berries and the Effects of Growth Substance Treatments, 1973, Plant Physiol. vol. 51, pp. 629-634.*
Chervin, C, Ethylene Seems Required for the Berry Development and Ripening in Grape, a Non-Climacteric Fruit, 2004, Ain Shams University Department of Horticulture, pp. 1-16.*
Hilt, C., Abscission of Grapevine Fruitlets in Relation to Ethylene Biosynthesis, 2003, Vitis, vol. 42, Issue 1, pp. 1-3.*
Delgado et al., "Influence of ABA and Ethephon Treatments on Fruit Composition of 'Tempranillo' Grapevines", Acta Hort. Aug. 2004, (ISHS) 640:321-326, Abstract.
S. Assmann "D6. Abscisic Acid Signal Transduction in Stomatal Responses", 2004, In: *Plant Hormones Biosynthesis, Signal Transduction, Action*! ed. Davies, p. 391-412.
Cutler, et al., "Formation and Breakdown of ABA", Dec. 1999, Trends in Plant Science vol. 4 No. 12, pp. 472-478.
Delgado et al., "Influence of ABA and Ethephon Treatments on Fruit Composition of 'Tempranillo' Grapevines", 2004, Acta Hort., 640, pp. 321-326.
During, H. et al., "Effects of Abscisic Acid and Benzyladenine on Irrigated and Non-Irrigated Grapevines", Feb. 20, 1980, Scientia Horticulturae 13: pp. 253-260.
Finkelstein et al., "Abscisic Acid Biosynthesis and Response", 2002. The *Arabidopsis* Book, American Society of Plant Biologists, pp. 1-52.
Han et al., "Effects of ABA and Ethephon Treatments on Coloration and Fruit Quality in 'Kyoho' Grape", 1996, J. Kor. Soc. Hort. Sci. 37(3), pp. 416-420.
Jensen et al., "Effect of Ethephon on Color and Fruit Characteristics of 'Tokay' and 'Emperor' Table Grapes", 1975, Am. J. Enol. Viticult., vol. 26, No. 2, pp. 79-81.
Jeong et al., "Effects of Plant Hormones and Shading on the Accumulation of Anthocyanins and the Expression of Anthocyanin Biosynthetic Genes in Grape Berry Skins", 2004. Plant Sci., vol. 167, pp. 247-252.
Kende et al., "The Five "Classical" Plant Hormones", Jul. 1997, The Plant Cell. vol. 9, pp. 1197-1210.
Kondo et al., Relation Between ABA Application and Fruit Quality of 'Pionnier' Grape (*Vitis* Sp.), 1998, Acta Hort., 464: 35-40.
Kull et al.., "Mixtures of Quaternary Ammonium Compounds and Long-chain Fatty Acids as Antifungal Agents", Apr. 17, 1961, Applied Microbiology vol. 9, pp. 538-541.
Lee et al., "Effect of Sucrose, Abscisic Acid, and Indoleacetic Acid on the Anthocyanin Development in 'Kyoho' Grape (*Vitis labruscana*)", 1980, J. Kor. Soc. Hort. Sci., 21(2), pp. 158-163.

(Continued)

*Primary Examiner* — John Pak
*Assistant Examiner* — Andriae M Holt
(74) *Attorney, Agent, or Firm* — Wood, Phillips, Katz, Clark & Mortimer

(57) ABSTRACT

This invention describes the use of S-abscisic acid (S-ABA) and ethylene producing-agents such as ethephon to synergistically improve red color in grapes and to alter the sensory characteristics of wine.

10 Claims, No Drawings

(56) References Cited

OTHER PUBLICATIONS

Lee et al., "Effects of Natural Type (S)-(+)-Abscisic Acid on Anthocyanin Accumulation and Maturity in 'Kyoho' Grapes", 1997, J. Kor. Soc. Hort. Sci. 38(6), pp. 717-721.
Mannini et al., "Effect of 2-Chloroethylphosphonic Acid (Ethephon) on the Endogenous Levels of Gibberellin-Like Substances and Abscisic Acid in Buds and Developing Shoots of Three Grape Varieties", 1982. Amer. J. Enol. Viticult. vol. 33 No. 3, pp. 164-167.
B. Milborrow, "Advanced Plant Physiology", 1984, Inhibitors, M.B. Wilkins (ed.), Pitman Publishing, London, England, pp. 76-110.
Peppi et al., "Abscisic Acid Application Timing and Concentration Affect Firmness, Pigmentation, and Color of 'Flame Seedless' Grapes", 2006, HortScience, 41(6), pp. 1440-1445.
Peppi et al., "Application Timing and Concentration of Abscisic Acid Affect the Quality of 'Redglobe' Grapes", 2007, Journal of Horticultural Science and Biotechnology, 82(2), pp. 304-310.
Peppi et al., "Timing and Concentration of Abscisic Acid Applications Affect the Quality of 'Crimson Seedless' Grapes", 2007, International Journal of Fruit Science, vol. 7(4), pp. 71-83.
Raschke et al., "Simultaneous and Independent Effects of Abscisic Acid on Stomata and the Photosynthetic Apparatus in Whole Leaves", 1985, Planta, 163, pp. 105-118.
Szyjewicz et al., "Ethephon ((2-Chloroethyl)phosphonic Acid, Ethrel, CEPA) in Viticulture—A Review", 1984, Am. J. Enol. Vitic., vol. 35 No. 3, pp. 117-123.
Byun et al., (English Translation) "Effects of GA3, thidiazuron and ABA on fruit set and quality of 'Kyoho' grapes" J. Kor. Soc. Hort. Sci., 1995, vol. 36, pp. 231-239.
Kim et al., (English Translation) "Effects of Ethephon and ABA Application on Sugar and Organic Acid Content in Grapes", Jour. Kor. Soc. Hort. Sci., 1998, 39(5), pp. 542-546.

* cited by examiner

SYNERGISTIC COMBINATION TO IMPROVE GRAPE COLOR AND TO ALTER SENSORY CHARACTERISTICS OF WINE

FIELD OF THE INVENTION

The present invention is directed to the use of a combination of S-abscisic acid (S-ABA) or its salts with an ethylene producing chemical such as ethephon, an ethylene biosynthesis precursor such as 1-aminocyclopropane-1-carboxylic acid (ACC), an ethylene mimic such as acetylene, or ethylene to improve red color in grapes and to alter the sensory characteristics of wine.

BACKGROUND OF THE INVENTION

Fruit color is an important quality factor in red table and wine grapes. Commercial harvest requires sufficient levels of color in commercially mature fruit and this can be a significant challenge for table grape growers. Fruit color development can be influenced by a number of factors including the grape cultivar, rootstock, plant vigor, climate, canopy management, light exposure, crop load, irrigation, fertilization, and plant growth regulators. Consequently, achieving optimal fruit color requires a programmatic approach rather than the use of a single tool or practice.

The plant growth regulator ethephon, an ethylene-releasing chemical, is one tool that can be used to help improve color development (Jensen et al., 1975; Szyjewicz et al., 1984). However, ethephon has shortcomings and risks. For example, in Crimson Seedless table grapes, ethephon efficacy is often inconsistent or poor. Multiple applications of high rates of ethephon may be required in order to achieve the desired level of coloration, if it can even be achieved. In addition to being inconsistent in its coloring effect, ethephon can cause berry softening, berry cracking or splitting and poor storage and shelf life (e.g. Jensen et al., 1975; Szyjewicz et al., 1984). Because of the importance of fruit color development, there is a need for additional tools to help improve grape coloration.

S-Abscisic acid (S-ABA) is a naturally occurring plant hormone found in all higher plants (Cutler and Krochko, 1999. Finkelstein and Rock, 2002). Levels of S-ABA in plants range from a few parts per billion in some aquatic plants to 10 parts per million in avocado fruit mesocarp (Milborrow, 1984). S-ABA is involved in many major processes during plant growth and development including dormancy, germination, bud break, flowering, fruit set, general growth and development, stress tolerance, ripening, maturation, organ abscission, and senescence. S-ABA also plays an important role in plant tolerance to environmental stresses, such as drought, cold, and excessive salinity.

One key role of S-ABA in regulating physiological responses of plants is to act as a signal of reduced water availability to reduce water loss, inhibit growth and induce adaptive responses. All these functions are related to stomatal closure of plant leaves (Raschke and Hedrich, 1985). When stomata close, plants conserve water to survive in environmental stresses. However, stomatal closure also results in the reduction of photosynthesis, and thus growth. Stomatal closure is a rapid response of plants to S-ABA. The mechanism of S-ABA that causes stomatal closure has been studied, and the effect has been shown to be primarily due to the effect of S-ABA on guard cell ion channels. Specifically, S-ABA blocks $H^+$ efflux from and $K^+$ influx into guard cells and promotes $K^+$, $Cl^-$, and malate efflux and $Ca^{2+}$ influx. The net effect of S-ABA is to reduce the total osmotica in the guard cells, which in turn decreases the water content in the cell. This causes the guard cells to lose their turgor and thus close the stomata (Assmann 2004). The closing of stomata results in reduced transpiration of the plant leaf. In grapes, application of S-ABA has been reported to increase stomatal resistance in grapevines, thereby reducing the gas exchange and stomatal transpiration of the leaves (Düring and Broquedis, 1980).

The exogenous application of S-ABA to red grapes prior to harvest has been shown to increase and accelerate the accumulation of anthocyanins and increase the red color of the grape berry skins (e.g. Han et al., 1996; Lee et al., 1997; Kondo et al., 1998; Pepe et al., 2006). S-ABA has been shown to be effective on red color varieties on which ethephon often is not commercially effective (e.g. Crimson Seedless). At very high rates, S-ABA may be associated with softened, split berries, or leaf yellowing.

The application of the plant growth hormones/plant growth regulators S-ABA and ethephon both stimulate development of red color by increased accumulation of anthocyanin pigment in the berries.

While both S-ABA and ethephon stimulate development of color, there are potential shortcomings with each material. Ethephon performance can be inconsistent, dependent upon such factors as cultivar, vineyard, year, and environmental conditions. High levels of ethephon are known to cause problems such as berry softening, berry splitting, and short shelf life (Jensen et al, 1975; Szyjewicz et al., 1984). S-ABA has not been registered and commercialized. Results from S-ABA field experiments show good efficacy, but response can sometimes be variable.

SUMMARY OF THE INVENTION

The present invention is directed to the preharvest treatment of grapes after fruit set with S-ABA or its salts and with an ethylene producing chemical such as ethephon, an ethylene biosynthesis precursor such as ACC, an ethylene mimic such as acetylene, or ethylene. This combination treatment program accelerates and improves development of red color in grape berries, resulting in a more rapid and consistent red color at lower rates compared to that which can be achieved with either compound applied alone at higher rates. Also, the use of the combination program at lower application rates lessens the risk of negative side effects that can occur with S-ABA or its salts and with ethylene-producing chemicals when these compounds are applied at higher rates. In addition, the combination program potentiates the positive effects of S-ABA on various sensory characteristics of wine quality.

DETAILED DESCRIPTION OF THE INVENTION

The present invention comprises the application of S-ABA or its salts and ethylene producing-agents such as ethephon or ethylene to grapes or grape vines to improve the development of red color and to alter various sensory characteristics of wine quality. S-ABA or a salt of S-ABA is applied to the grapevines by foliar spray including electrostatic spray application to the grape berries and leaves, by application to the roots of the grapevine through irrigation or fertigation methods, or by injection into the grapevine. An ethylene producing-agent, ethylene biosynthesis precursor, ethylene mimic, or ethylene is applied to the grapevines by foliar spray application to the grape berries and leaves.

Experiments were conducted in which S-ABA and ethephon were applied to grapes alone or together, both as tank mix applications and sequential applications. Application of S-ABA and ethephon together at the same time or separately in a sequential application program results in a novel, non-obvious effect in which more effective red coloration is achieved and lower rates of one or both compounds are used. Also, the application of ethephon with S-ABA on wine grapes potentiates the positive effects of S-ABA on various sensory characteristics of wine quality.

Combination treatments utilizing lower rates of either or both S-ABA and ethephon result in better coloration than can be achieved with either compound alone at higher rates.

Combination treatments utilizing lower rates of either or both compounds give more effective, reliable, and more cost effective grape coloration.

Combination treatments utilizing lower rates of either or both compounds safen grape coloration programs, minimizing potential negative effects often associated with ethephon and that are sometimes associated with high rates of S-ABA.

Although ethephon itself does not have a positive effect on sensory characteristics of wine quality, the combination of S-ABA and ethephon gives higher quality wine than that achieved with S-ABA alone.

Abscisic acid (S-ABA; S-(+)-abscisic acid; +-ABA, (+)-(S)-cis,trans-abscisic acid, (+)-(S)-cis,trans-ABA; S-ABA; (S)-5-(1-hydroxy-2,6,6,-trimethyl-4-oxo-2-cyclohexen-1-yl)-3-methyl-(2Z,4E)-pentadienoic acid; CAS registry no. [21293-29-8]) is available from Lomon BioTechnology Co., Ltd. (Shichuan, China).

Suitable salts of S-ABA include, but are not limited to sodium, potassium, calcium, ammonium, magnesium, and amine salts.

Ethephon is available from Bayer CropScience (GmbH, Frankfurt am Main, Germany).

S-ABA and ethephon are applied to the grapevines after berry set to achieve the desired effect on coloration of the grape berries and on the sensory characteristics of grape berries and wine. The presently preferred timing of the S-ABA application is during the period of pre-veraison (approximately three weeks prior to veraison, where veraison is defined as the beginning of berry softening) through the post-veraison period until approximately one week prior to harvest.

Water is used as the carrier solvent for the applications. In the present invention, surfactants can be added to the chemical solution to improve the performance of the S-ABA or its salts, particularly for the foliar application. The water solution may contain between 0.01% to 0.5% v/v of a surfactant.

The presently preferred surfactant for S-ABA and S-ABA salt performance is Brij 98 (polyoxyethylene (20) oleyl ether) available from Uniqema (Castle, Del.). Other surfactants are also useful in the present invention, including but not limited to, other surfactants in the Brij family (polyoxyethylene fatty alcohol ether) available from Uniqema (Castle, Del.), surfactants in the Tween family (Polyoxyethylene sorbitan ester) available from Uniqema (Castle, Del.), the Silwet family (Organosilicone) available from Momentive Performance Materials (Wilton, Conn.), the Triton family (Octylphenol ethoxylate) available from The Dow Chemical Company (Midland, Mich.), the Tomadol family (ethoxylated linear alcohol) available from Tomah3 Products, Inc. (Milton, Wis.), the Myrj family (Polyoxyethylene (POE) fatty acid ester) available from Uniqema (Castle, Del.), the Span family (Sorbitan ester) available from Uniqema (Castle, Del.), and the Trylox family (Ethoxylated Sorbitol and Ethoxylated Sorbitol Ester) available from Cognis Corporation (Cincinnati, Ohio) as well as commercial surfactants such as Latron B-1956 (77.0% modified phthalic/glycerol alkyl resin and 23.0% Butyl alcohol) available from Dow AgroSciences LLC (Indianapolis, 1N), Capsil (Blend of Polyether-polymethylsiloxane copolymer and nonionic surfactant) available from Aquatrols (Paulsboro, N.J.), Agral 90 (Nonyl phenol ethoxylate) available from Norac Concept. Inc. (Orleans, Ontario, Canada), Kinetic (99.00% proprietary blend of polyalkyleneoxide modified polydimethylsiloxane and nonionic surfactants) available from Setre Chemical Company (Memphis, Tenn.), and Regulaid (90.6% 2-butoxyethanol, poloxalene, monopropylene glycol) available from KALO, Inc. (Overland Park, Kans.).

Other additives are also useful in the present invention including, but not limited to, urea, nitrate salts such as ammonium nitrate, salts such as calcium chloride, humectants such as poly(ethylene glycol), and vegetable oils such as soybean oil, corn oil, cotton oil, and palm oil.

The effective dose range of the active ingredient S-ABA varies depending on the water volume applied as well as other factors such as the plant variety, size, age, and application method. The S-ABA dose range is from 1 to 800 mg/vine. The preferred S-ABA dose range for application is 20 to 400 mg/vine. The preferred application volume for application is 5 to 400 gallons/acre. Foliar spray applications are directed at the grape bunches to achieve complete coverage of the grape bunches and to maximize the effect of the S-ABA application. Foliar spray applications include, but are not limited to airblast spray application or electrostatic spray application. Soil applications are directed towards the rooting zone. Application methods include, but are not limited to application through irrigation/fertigation dripper line or application of S-ABA formulations or solutions to the soil at the base of the vine, followed by application of water to the soil to transport the S-ABA to the roots of the vine. The preferred application timing for S-ABA is during the period from veraison through 1 week before harvest.

The ethephon dose range is 1 to 800 mg/vine. The preferred ethephon dose range is 20 to 400 mg/vine. The preferred application volume is 5 to 400 gallons/acre. Foliar applications are directed at the grape bunches. The preferred application timing for ethephon is the period from veraison through 1 week before harvest.

The invention is demonstrated by following representative examples.

EXAMPLES

Example 1

Plant material and application: A replicated field experiment was conducted on the red table grape cultivar 'Crimson Seedless' in the Central San Joaquin growing region of California, United States to evaluate the synergistic effect of S-ABA and ethephon on grapes. The vineyard was 12 years old and on overhead trellis with a vine spacing of 12 ft by 7 ft (518 vines/acre). Plot size was three vines/replicate, with six replicates/treatments. The area evaluated within each plot was one center vine and two half vines on each side for a total of two vines. Applications were made seven days after veraison (beginning of berry softening). On the day of application, red coloration was developing on about 10% of the berries.

The nine treatments applied were control, S-ABA alone (88, 292, or 877 mg/vine), ethephon alone (88, 292, or 877 mg/vine), and combinations of S-ABA and ethephon (88 mg/vine S-ABA and 88 mg/vine ethephon or 292 mg/vine S-ABA and 292 mg/vine ethephon). All treatments were mixed with the adjuvant Latron B-1956 (0.05% v/v; Dow AgroSciences LLC, Indianapolis, Ind.). Treatments were applied with a backpack mist blower at 200 gallons/acre (757 l/acre).

Evaluations: The total grape clusters were counted on the day of application. After treatment, the plots were evaluated weekly for color development by counting the number of harvestable colored grape clusters in each plot. All harvestable colored clusters were removed 79 days later to eliminate over-mature clusters. The number of harvestable colored grape clusters was expressed as cumulative harvestable clusters (number of harvestable clusters per two vines). Average berry firmness, weight and Brix (soluble solids) were evaluated 5 days later. Evaluation samples consisted of 10 second shoulders (second lateral branch of the main rachis) from 10 different clusters selected randomly from each plot. All berries in the evaluation samples were removed, counted, and weighed. A sub-sample of 20 to 30 berries was crushed for brix (soluble solids) analysis. Brix was measured with a hand-held temperature compensating Leica Refractometer. An additional 10 berries were selected randomly for berry firmness. Berry firmness was determined by a hand held Wilson Penetrometer (0 to 1000 g) mounted on a stand with a 6 mm tip.

TABLE 1

Effect of S-ABA and ethephon alone and in combination on Crimson Seedless grape number of cumulative harvestable clusters, firmness, Brix, and berry weight at harvest. Applications were made at veraison plus seven days.

| S-ABA (mg/vine) | Ethephon (mg/vine) | Cumulative harvestable clusters (no. per two vines) | Firmness (g) | Berry weight (g) | Brix (degrees) |
|---|---|---|---|---|---|
| 0 | 0 | 7.3 | 850 | 4.9 | 19.0 |
| 88 | 0 | 11.8 | 766 | 5.0 | 20.0 |
| 292 | 0 | 38.0 | 759 | 5.4 | 19.5 |
| 877 | 0 | 43.8 | 663 | 6.1 | 19.1 |
| 0 | 88 | 9.2 | 765 | 5.2 | 20.6 |
| 0 | 292 | 15.7 | 766 | 5.8 | 20.3 |
| 0 | 877 | 40.2 | 709 | 5.4 | 20.1 |
| 88 | 88 | 24.7 | 781 | 5.5 | 19.9 |
| 292 | 292 | 50.2 | 710 | 5.4 | 19.4 |

S-ABA alone and ethephon applied alone to Crimson Seedless grape both increased the cumulative harvestable cluster number in dose-dependent manners for both compounds (Table 1). Thus, for S-ABA: Cumulative harvestable clusters=12.5+(S-ABA (mg/vine)*0.056); $r^2$=0.75 and for ethephon: Cumulative harvestable clusters=6.1+(ethephon (mg/vine)*0.040); $r^2$=0.99. However, the combination treatment of 88 mg/vine S-ABA and 88 mg/vine ethephon yielded a surprisingly high number of cumulative harvestable clusters (24.7 harvestable clusters) compared to either compound alone at 88 mg/vine (11.8 or 9.2 harvestable clusters for S-ABA alone or ethephon alone, respectively).

Synergy was determined by an industrially accepted method (Kull et al., 1961, Applied Microbiology 9:538-541 and Robertson and Ramesh, 1998, U.S. Pat. No. 5,716,629). Synergy Index=Qa/QA+Qb/QB where:

Qa=dose of compound A in mg/vine, in the mixture, which produced an end point

QA=dose of compound A in mg/vine, acting alone, which produced an end point.

Qb=concentration of compound B in mg/vine, in the mixture, which produced an end point.

QB=dose of compound B in mg/vine, acting alone, which produced an end point.

Synergy, additivity, or antagonism are shown when the Synergy Index is less than one, equal to one, or greater than one, respectively. The Synergy Index was calculated for the combination treatment of 88 mg/vine each of S-ABA and ethephon with an end point of 24.7 cumulative harvestable clusters. The calculated Synergy Index for this combination treated is 0.44 ($88/337+88/484$). Since the Synergy Index for this combination is less than one, the combination is synergistic.

The combination treatment of 292 mg/vine each of S-ABA and ethephon yielded the highest number of cumulative harvestable clusters (50.2) of all treatments including S-ABA or ethephon at the highest rate of 877 mg/vine (43.8 and 40.2, respectively).

Berry firmness for combination treatments of 88 or 292 mg/vine each of S-ABA and ethephon (781 or 710 g, respectively) was greater than or equal to the firmness of the highest rates of S-ABA or ethephon (663 or 709 g, respectively; Table 1). Thus, the combination treatments did not lead to excessive losses in berry firmness.

Berry weights and brix were greater for all S-ABA and ethephon treatments than the control (Table 1). Thus, the combination treatments did not reduce berry size or brix compared to the control.

Example 2

A replicated field experiment was conducted on the red wine grape cultivar 'Cabernet Sauvignon' in the Riverland growing region of South Australia. The vineyard was 19 years old with a vine spacing of 3 m by 3 m. The plot size was nine vines/replicate with three replicates/treatment. S-ABA (200 ppm) and ethephon (200 ppm) were foliar applied to Cabernet Sauvignon grapes at 50-60% veraison using a commercial airblast sprayer. Treatments were mixed with the adjuvant Agral 600 (10 mL/100 L v/v; CropCare Australasia, Pty Ltd.).

Ethephon alone had little effect on sugar levels (Be), pH, titratable acidity, or anthocyanins of grapes measured at commercial harvest (Table 2). Ethephon alone increased wine color density and phenolics. S-ABA alone had little effect on sugar levels (Be), pH, or titratable acidity. In this experiment, grape anthocyanins at harvest and wine color density levels in the S-ABA treatment were lower than in the untreated. S-ABA treated wine received a higher wine assessment score by a trained wine tasting panel. Although ethephon alone did not affect wine assessment scores, the ethephon and S-ABA combination treatment increased wine color density and phenolics more than S-ABA or ethephon alone and the wine received the most favorable wine assessment score by the trained wine tasting panel. Thus, although ethephon had no effect on wine quality by itself, ethephon surprisingly potentiated the positive effect of S-ABA on the sensory characteristics of wine.

TABLE 2

Effect of ethephon, S-ABA, and ethephon/S-ABA combination on Cabernet Sauvignon grape and wine quality.

| | Grapes at harvest | | | | Wine | Wine | Wine |
| --- | --- | --- | --- | --- | --- | --- | --- |
| | Be | pH | Titratable acidity | Anthocyanins (mg/g) | color density | Wine phenolics | Wine assessment[1] |
| Untreated | 12.9 | 3.9 | 4.9 | 0.91 | 7.2 | 21.9 | 2.4 |
| Ethephon (200 ppm) at veraison | 13.1 | 3.9 | 4.9 | 0.91 | 8.0 | 27.1 | 2.3 |
| ABA (200 ppm) at veraison | 12.4 | 4.0 | 4.6 | 0.78 | 5.6 | 20.2 | 2.7 |
| Ethephon + ABA at veraison | 12.9 | 4.0 | 4.7 | 0.94 | 8.7 | 29.4 | 3.1 |

[1]Assessment made from 5 characteristics - Color intensity, aroma intensity, body/fullness, flavor intensity, finish. Provisor Pty Ltd wine tasting panel scores.

The invention claimed is:

1. A method of increasing cumulative harvestable clusters in red grapes comprising applying a synergistic amount of S-abscisic acid or its salts and ethephon to red grapes after veraison, wherein the amount of S-abscisic acid is from 88 to 292 mg/vine, the amount of ethephon is from 88 to 292 mg/vine, and the application volume is 5 to 400 gallons/acre.

2. The method of claim 1 wherein the amount of S-abscisic acid or its salts is 88 mg/vine.

3. The method of claim 1 wherein the amount of S-abscisic acid or its salts is 292 mg/vine.

4. The method of claim 1 wherein the amount of ethephon is 88 mg/vine.

5. The method of claim 1 wherein the amount of ethephon is 292 mg/vine.

6. The method of claim 1 wherein the S-abscisic acid salt is selected from the group consisting of sodium, potassium, calcium, ammonium, magnesium, and amine salts.

7. The method of claim 1 wherein the S-abscisic acid or its salts is applied by foliar spray, irrigation, or fertigation.

8. The method of claim 7 wherein the S-abscisic acid or its salts is applied by foliar spray.

9. The method of claim 7 wherein the S-abscisic acid or its salts is applied by irrigation.

10. The method of claim 7 wherein the S-abscisic acid or its salts is applied by fertigation.

* * * * *